United States Patent [19]

Malkamäki

[11] Patent Number: 5,050,615
[45] Date of Patent: Sep. 24, 1991

[54] METHOD FOR THE DETERMINATION OF A GAS COMPONENT CONTENT IN THE RESPIRATORY GAS OF A PATIENT

[75] Inventor: Lauri Malkamäki, Vantaa, Finland
[73] Assignee: Instrumentarium Corp., Finland
[21] Appl. No.: 400,076
[22] Filed: Aug. 29, 1989

[30] Foreign Application Priority Data

Sep. 2, 1988 [FI] Finland .................................. 884048

[51] Int. Cl.$^5$ .............................................. A61B 5/08
[52] U.S. Cl. .................................... 128/719; 128/720; 128/725
[58] Field of Search ................ 128/719, 716, 720, 725, 128/633, 664; 73/23, 23.1, 24, 25, 863.01–863.03, 863.31, 863.33, 863.81–863.83

[56] References Cited

U.S. PATENT DOCUMENTS

| 3,661,528 | 5/1972 | Falk | 73/865.01 |
|---|---|---|---|
| 3,910,261 | 10/1975 | Ragsdale | 73/863.01 |
| 4,248,245 | 2/1981 | Kempin | 73/863.01 |
| 4,361,027 | 11/1982 | Schmitt | 73/863.81 |
| 4,619,269 | 10/1986 | Cutler et al. . | |
| 4,799,374 | 1/1989 | Bossart et al. | 73/863.01 |
| 4,799,394 | 1/1989 | Barnett et al. | 73/863.01 |
| 4,800,763 | 1/1989 | Hakkers et al. | 73/863.81 |

FOREIGN PATENT DOCUMENTS

| 1915959 | 10/1970 | Fed. Rep. of Germany . | |
| 67997 | 3/1985 | Finland . | |
| 829409 | 3/1960 | United Kingdom | 128/719 |
| 2084321 | 4/1982 | United Kingdom | 128/719 |
| 2142722 | 1/1985 | United Kingdom | 73/863.01 |

Primary Examiner—Randall L. Green
Assistant Examiner—K. M. Reichle
Attorney, Agent, or Firm—Andrus, Sceales, Starke & Sawall

[57] ABSTRACT

The invention relates to a method for the determination of the content of one or a plurality of gas components, e.g. carbon dioxide, present in the respiratory gas of a patient, especially in small children whose respiration is characterized by a high respiration frequency and a small respiration volume. The method is based on sucking, e.g. by means of a pump (8), into a tube (5) samples of the respratory gas of a patient from the phase of a respiratory cycle that is considered appropriate. In the determination of carbon dioxide content, the sampling is preferably effected as of the instant at which a flow reversal detector (4) fitted in tube (2) detects that a patient is inhaling or when the corresponding reverasl of flow has been detected in a respirator (3). In the determination of carbon dioxide content, the sampling must be stopped before the boundary zone of fresh incoming gas and exhaled gas, in inhalation reaches the end of sampling tube (5). Immediately after the preceding sample it is possible to suck into tube (5) the samples picked up from the following respirartory cycles. Thus, there may be a plurality of samples in successive order in tube (5) prior to their arrival at a gas component content measuring element (6).

18 Claims, 1 Drawing Sheet

METHOD FOR THE DETERMINATION OF A GAS COMPONENT CONTENT IN THE RESPIRATORY GAS OF A PATIENT

BACKGROUND OF THE INVENTION

The present invention relates to a method for the determination of the content of one or more gas components in the respiratory gas of a patient on the basis of samples picked up from a plurality of respiratory cycles, several successive samples being accommodated in the same sample chamber prior to the actual determination. An apparatus used in such determination comprises a tube to be placed in the windpipe and provided with a means detecting the reversal of a respiratory gas flow and/or or of a respiration device. The apparatus also includes a sampling tube provided with a means measuring the content, of a gas component, a valve and a pump or a reduced pressure chamber and a control means controlling the operation of such elements. This method is particularly useful for finding out the content of a gas component or gas components in the exhalation gases of small children, such as newborn babies, since small children have a high respiration frequency and a small respiration volume. The most notable gas component to be measured is carbon dioxide.

Measurements of the carbon dioxide content in the exhalation gases of a patient have been effected by continuously pumping a sample from the exhalation gases to a $CO_2$-sensor. In adults, this method is capable of providing reasonably good results over the entire breathing cycle but in small children, reliable measurement of the final $CO_2$-content in exhalation gases has not been possible due to a high respiratory frequency and a small respiratory volume. The small respiratory volume provides a very small sample that must be carried along a lengthy tube to a $CO_2$-sensor. Inevitably, other gases along with exhalation gases will enter the tube, the mixing and dead space having a substantial effect on the measurement. Thus, the test results become distorted and provide an incorrect indication of the carbon dioxide level. Therefore, this method cannot be applied to small children.

The determination of the final $CO_2$-content in exhalation gases is possible by using a miniaturized sensor which is placed immediately adjacent to the head of a patient. However, dead space is a problem also in this method. Another drawback is the high cost of this method and it is also inconvenient to apply in case of small children.

An object of this invention is to eliminate the above drawbacks. The object is to provide a reliable determination method for one or a plurality of gas components in the respiratory or alveolar gas of a patient and particularly infant patients, whereby a small respiratory volume and a high respiratory frequency are not a problem. Another object is to provide a method which is easy to operate, pleasant to a patient and economical in terms of equipment costs.

The characterizing features of the invention are set forth in the annexed claims.

DETAILED DESCRIPTION OF THE DRAWING

Figure 1:
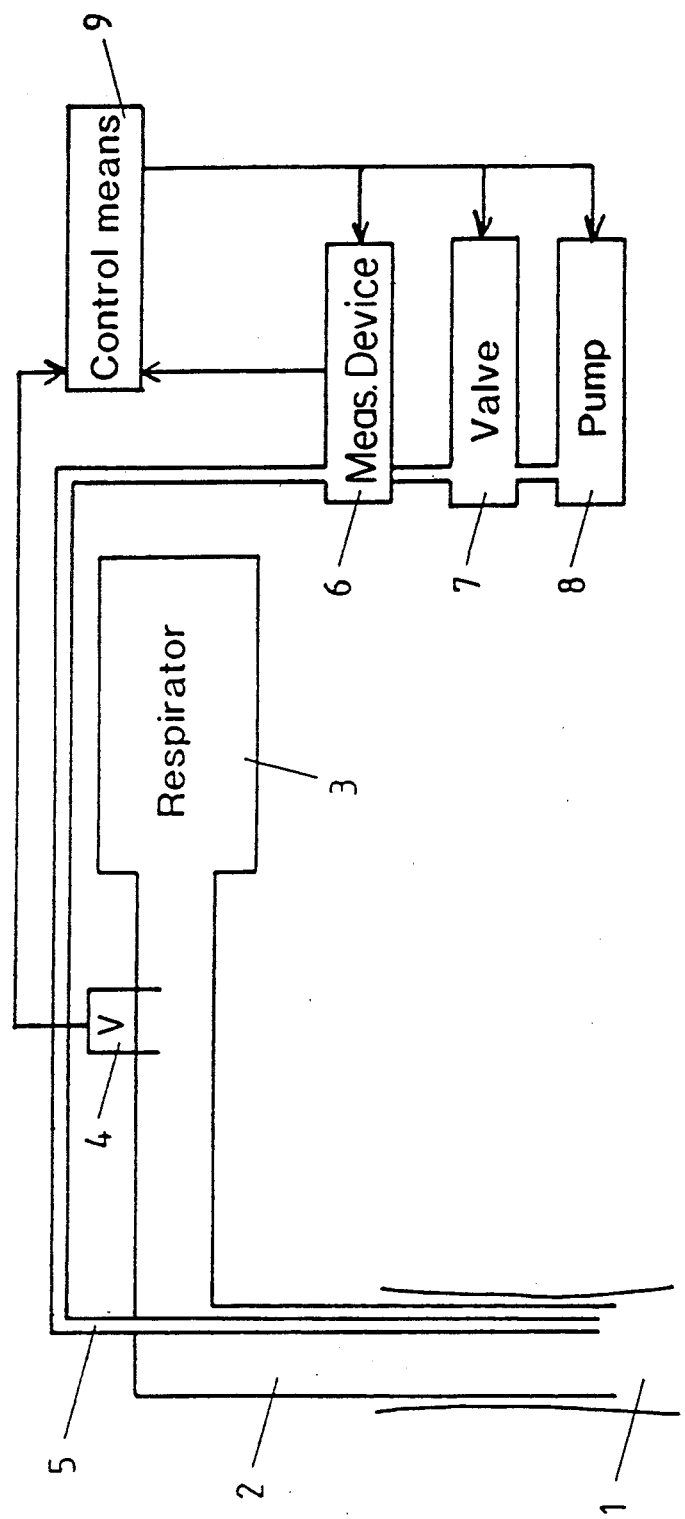

The invention will now be described in more detail with reference made to the accompanying drawing, in which FIGURE 1 shows a diagrammatic view of an apparatus used for determining the content of one or a plurality of gas components in respiratory gas in accordance with the invention.

DETAILED DESCRIPTION OF THE PREFERRED EMBODIMENT

Referring to FIG. 1, a tube 2, often referred to as an intubation tube, has been inserted in a patient's windpipe 1. The other end of the intubation tube leads to a respirator 3 which may be a conventional commercially available device. Tube 2 is fitted with a means 4 detecting the reversal of the direction of flow.

Inside tube 2 runs another tube or tubing 5, one end of which lies preferably adjacent to the end of intubation tube 2 in the windpipe. The other end of tube 5 leads to an element 6 measuring the content of a gas component in the respiratory gas. Such elements are commercially available. Downstream of element 6 lies a valve 7 and a pump 8. Valve 7 is opened and closed to control the pick-up of samples into tube 5 and the passing of samples to said gas component measuring element 6. A control means 9, preferably a microprocessor, in turn controls the opening and closing of valve 7 on the basis of data received from said means 4 detecting the reversal of flow. Also the data coming from the gas component content measuring element 6 are supplied to the control means.

In the case shown in FIG. 1, pump 8 draws a small sample charge of exhalation gases along a tube 5 fitted inside an intubation tube 2. A sample required in the determination of carbon dioxide content is preferably picked up from the exhalation gas as of the instant the reversal of gas flow is detected by means 4, i.e. at the moment the patient begins inhalation. The length, or amount of a sample in tube 5 can be related either to the volume of flowing gas or to a time determined experimentally. The sampling must be stopped before the boundary zone of fresh incoming gas and exhaled carbon dioxide containing gas reaches the end of sample tube 5 during inhalation. Following exhalation cycles are similarly sampled by sucking the samples into tube 5 after the preceding samples. Thus, tube 5 can accommodate a plurality of separate samples at the same time. The number of samples depends on the length and internal diameter of tube 5. The samples arrive at carbon dioxide content measuring element 6, which is an infrared spectrophotometer, after a slight delay. When samples are picked up from a sufficient number of exhalation cycles, the final $CO_2$-content of exhalation gas can be reliably measured.

In the sampling method, a sampling tube and a measuring chamber, can have a volume of, e.g., 2.5 ml and a suitable sampling rate of, e.g., 150 ml/min. Thus, the system throughput time is circa one second. A suitable sample suction time would be 0.1–0.2 seconds, the total delay being accordingly 10–5 respiratory cycles, respectively. Thus, the delay would be clinically negligible, i.e. circa 5–10 seconds.

The suction time of pump 8 is set by opening and closing valve 7, preferably a solenoid valve, under the control of control means 9. The pump can be preferably kept in operation over the entire measuring process, whereby the suction of gas through valve 7 occurs accurately and sharply. The pump can also operate periodically only when necessary.

The flow reversal detecting means 4 can be, e.g., a flow sensor, a pressure sensor, a thermistor or some other prior known solution, such as a signal coming from a respirator. Such elements are commercially available.

Referring to the drawing, there is shown just one possible embodiment but various other embodiments are available within the scope of the claims.

The measuring method shown in FIG. 1 can be applied just as well to other gas components, such as oxygen, present in the respiration of a patient. In this case, the carbon dioxide content measuring element 6 would be replaced with an element measuring this particular gas component. Naturally it is also possible to measure simultaneously more than one gas component in exhalation air.

Depending on a gas component to be measured, a sample is picked up from a desired certain phase, either from exhalation or inhalation gas.

Tube 2 can run by way of the mouth of a patient into the windpipe of a patient or, with tracheostomy patients, directly through the throat into the windpipe. The respirator 3 is not necessary. The main point is that a patient breathes through tube 2 from which a sample is picked up in tube 5. Tube 5 can of course run in the windpipe outside tube 2.

Valve 7 can also be located upstream of the gas component content measuring element 6. In terms of the invention, the disposition of various pieces of equipment is not significant.

The suction of samples into tube 5 can be effected by means of pump 8 or by some other technique, such as vacuum.

Instead of an infrared spectrophotometer, said gas component content measuring element 6 can be, e.g., some other spectrophotometer or some other suitable gas analyzer.

In addition to a solenoid valve, suitable valves include, e.g., a piezoelectric or magnetostrictive valve or other prior known structure.

I claim:

1. A method for determining the content of one or more gaseous components in the gas exhaled by a patient in the course of respiration, the respiration occurring in cycles, said method comprising the steps of:
   withdrawing a sample of the respiratory gas exhaled by a patient during a respiratory cycle of the patient, the withdrawal occurring at a sampling location;
   moving the withdrawn sample incrementally away from the sampling location toward an analysis location;
   repeating the withdrawing and moving steps, whereby the moving step becomes one of simultaneously, incrementally moving a plurality of successively withdrawn, respiratory gas samples in seriatim toward the analysis location; and
   determining the gaseous component content of the gas exhaled by the patient from the respiratory gas samples at the analysis location.

2. The method according to claim 1 wherein the withdrawing step is further defined as withdrawing a sample from each of a plurality of successive respiratory cycles.

3. The method according to claim 1 wherein the respiratory cycle of the patient has a plurality of phases, and wherein the withdrawing step is further defined as withdrawing a sample during a desired phase of the respiratory cycle.

4. The method according to claim 3 wherein bidirectional inhalation-exhalation gas flow occurs in the course of the patient's respiratory cycles and wherein the withdrawing step is further defined as withdrawing a sample responsive to the directional properties of the gas flow.

5. The method according to claim 4 wherein bidirectional inhalation-exhalation gas flow can occur at the sampling location and wherein the withdrawing step is further defined as terminating the withdrawing of a sample before fresh inhalation gas flow occurs at the sampling location.

6. The method according to claim 4 wherein the withdrawing step is further defined as withdrawing a sample responsive to a reversal of the gas flow direction.

7. The method according to claim 6 further defined as including the step of sensing the reversal of the gas flow direction by one of a flow sensor, a pressure sensor, or a thermistor.

8. The method according to claim 3 wherein the withdrawing step is further defined as withdrawing a sample responsive to the operation of a respirator coupled to the patient.

9. The method according to claim 3 wherein the withdrawing step is further defined as withdrawing a sample as the patient commences inhalation.

10. The method according to claim 1 wherein the withdrawing step is further defined as withdrawing a sample by inserting a sampling device in the respiratory gas stream of the patient and by reducing the pressure in the sampling device to draw a respiratory gas sample into the device.

11. The method according to claim 10 further defined as reducing the pressure for a predetermined period of time to obtain the sample.

12. The method according to claim 10 further defined as establishing a reduced pressure and selectively applying the reduced pressure to the sampling device to withdraw a sample.

13. The method according to clam 10 wherein bidirectional gas flow occurs in the course of the patient's respiratory cycles and wherein the step of reducing the pressure is further defined as reducing the pressure in the sampling device responsive to a reversal of the gas flow direction.

14. The method according to claim 1 wherein the step of determining the gaseous component content is further defined as analyzing the spectral properties of the respiratory gas samples.

15. The method according to claim 1 wherein the determining step is further defined as one for determining gaseous component comprising the carbon dioxide or oxygen components in the gas exhaled by a patient.

16. The method according to claim 1 wherein the gas exhaled by the patient passes through a tube having ends and wherein the withdrawing step is further defined as withdrawing a sample adjacent an end of the tube.

17. The method according to claim 16 wherein the tube has an end lying in the windpipe of the patient and wherein the withdrawing step is further defined as withdrawing a sample adjacent the end of the tube in the windpipe of the patient.

18. A method for determining the content of one or more gaseous components in the gas exhaled by an infant or child patient in the course of respiration, the respiration occurring in cycles, said method comprising the steps of:

passing the gas exhaled by the patient through a tube lying in the windpipe of the patient;

withdrawing a sample of the respiratory gas exhaled by the patient from the tube during a respiratory cycle of the patient;

moving the withdrawn sample incrementally away from the tube toward an analysis location;

repeating the withdrawing and moving steps, whereby the withdrawing step becomes one of withdrawing a sample from each of a plurality of successive respiratory cycles of the patient and whereby the moving step becomes one of simultaneously, incrementally moving a plurality of successively withdrawn, respiratory gas samples in seriatim away from the tube toward the analysis location; and determining the gaseous component content of the gas exhaled by the patient from the respiratory gas samples at the analysis location.

* * * * *